United States Patent [19]

Brodeur et al.

[11] Patent Number: 5,013,664

[45] Date of Patent: May 7, 1991

[54] **COMMON PROTEIN OF *HAEMOPHILUS INFLUENZAE* TYPE B IDENTIFIED BY A MONOCLONAL ANTIBODY**

[76] Inventors: Bernard R. Brodeur, #404-50 Emmerson, Ottawa, Ontario, Canada, K1Y 4P7; Josee Hamel, 11 Juniper, Aylmer, Quebec, Canada, J9H 5Y8; Serge Montplaisir, Hôspital Sainte-Justine, Department of Microbiology and Immunology, 3175, Côte Sainte-Catherine, Montreal, Quebec, Canada, H3T 1C5

[21] Appl. No.: 867,510

[22] Filed: May 28, 1986

[51] Int. Cl.⁵ ................. C12N 5/12; C07K 15/78; G01N 33/53; G01N 33/535

[52] U.S. Cl. ................. 435/7.32; 530/387; 530/350; 435/240.2; 435/70.21; 435/7; 435/810; 435/851; 435/948; 435/240.27; 935/104; 935/100; 935/188; 935/110; 436/548

[58] Field of Search .................. 530/387, 350; 435/240.2, 240.27, 68, 7, 810, 851, 948; 935/104, 100, 108, 110; 436/548

[56] References Cited

U.S. PATENT DOCUMENTS 4,455,296 6/1984 Hansen et al. ............ 424/87

OTHER PUBLICATIONS

Hamel, J. et al. "A Monoclonal Antibody Identifying a Common Epitope of *Haemophilus influenzae* type b;" Hybridoma 5(1): 66, 1986.

Robertson, S. M. et al. "Monoclonal Antibodies Directed Against a Cell Surface-Exposed Outer Membrane Protein of *Haemophilus influenzae* Type b," Infect. Immun. 36(1): 80-88, Apr. 1982.

Johnston et al., "The Serological Classification of *Neisseria Gonorrhoeae*," The Journal of Experimental Medicine, vol. 143; 1976, pp. 741-758.

de St. Groth et al., "Production of Monoclonal Antibodies . . . ", Journal of Immunological Methods, 35 (1980), pp. 1-21.

Brodeur et al., "Parameters Affecting Ascites Tumour Formation . . . ", Journal of Immunological Methods, 71 (1984) pp. 265-272.

Brodeur et al., "Enzyme-Linked Immunosorbent Assay with Polyvalent Gonococcal Antigen", The Journal of Medical Microbiology; vol. 15, No. 1, pp. 1-9.

Laemmli, "Cleavage of Structural Proteins . . . ", Nature; vol. 227, Aug. 15, 1970, pp. 680-685.

Weber et al., "The Reliability of Molecular Weight Determinations . . . ", The Journal of Biological Chemistry; vol. 244, No. 16, Aug. 25, 1969, pp. 4406-4412.

Towbin et al., "Electrophoretic Transfer of Proteins . . . ", Proc. Natl Acad Sci U.S.A.; vol. 76, No. 9, 1979, pp. 4350-4354.

Bayer et al., "Insolubilized Biotin for the Purification of Avidin," pp. 265-267.

Macone et al., "Comparison of a New, Rapid, Enzyme-Linked Immunosorbent Assay . . . ", Journal of Clinical Microbiology, May 1985, vol. 21; No. 5, pp. 711-714.

Yolken, "Enzyme Immunoassays for the Detection of Infectious Antigens . . . "; Reviews of Infectious Diseases, vol. 4, No. 1, Jan.-Feb. 1982, pp. 35-68.

Gulig et al., "Coprecipitation of Lipopolysaccharide . . . "; Infection and Immunity, Sep. 1985, vol. 49, No. 3, pp. 819-827.

*Primary Examiner*—Margaret Moskowitz
*Assistant Examiner*—Paula Hutzell
*Attorney, Agent, or Firm*—Hoffman, Wasson & Gitler

[57] ABSTRACT

Monoclonal antibodies, and cell lines producing them, which show specificity for surface components of *Haemophilus influenzae* type b have been developed. These monoclonal antibodies may be used in methods and kits for detecting *H. influenzae* type b and antigens of *H. influenzae* type b and for purification of outer membrane protein to be used as vaccine.

13 Claims, No Drawings

COMMON PROTEIN OF *HAEMOPHILUS INFLUENZAE* TYPE B IDENTIFIED BY A MONOCLONAL ANTIBODY

BACKGROUND OF THE INVENTION

This invention relates to a monoclonal antibody (MAb) directed against a serotype-specific outer membrane protein of *Haemophilus influenzae* type B, a cell line producing the antibody, the purified outer membrane protein and the use of such an antibody or antigen for serotyping, diagnostic and vaccine purposes.

*H. influenzae* type b is the most common cause of meningitis in children under one year old. The recent emergence and rapid spread of antibiotic resistant strains, particularly those resistant to ampicillin, are causing special problems in treatment. Chemoprophylaxis with rifampin has given encouraging results by reducing the incidence of nasopharyngeal carriage but such an approach has only limited application. Early treatment is essential to prevent complications. A reliable and rapid test is important for identification of the infectious agent after the antibiotic treatment has begun and when viable bacteria are no longer detectable in body fluids. Several immunoassays using polyclonal antisera have been adopted for bacterial antigen detection. They have all shown either poor specificity and/or sensitivity.

Outer membrane proteins (OMPs) found on the cell surface of many gram-negative bacteria have been used in serotyping and immunoprotection studies. The OMPs of *H. influenzae* type b have received increasing interest as epidemiological markers and as potential vaccinogens for young children. The identification of a common surface antigen for *H. influenzae* type b has been hampered by the antigenic variability of the OMPs. The advent of MAbs provides the opportunity to analyse the *H. influenzae* type b surface components with improved accuracy and reproducibility.

U.S. Pat. No. 4,474,758 (inventor: J. S. C. Kuo; issued: 2 Oct. 1984) is concerned with a combined vaccine having two components: *Haemophilus influenzae* type B and pertussis outer membrane components.

U.S. Pat. No. 4,455,296 (inventors: E. J. Hansen et al; issued: 19 June 1984) is concerned with hybrid cell lines producing monoclonal antibodies directed against *Haemophilus influenzae* type b. The most useful monoclonal antibody, 6A2, showed activity against four out of six *H. influenzae* type b strains tested. Later studies by P. A. Julig and E. J. Hansen, published in Infection and Immunity, 49 (3), 819–827 (1985), indicate that this 6A2 monoclonal antibody is actually directed against a lipopolysaccharide (LPS) associated with the 39K outer membrane protein (OMP) of *H. influenzae* type b (the interaction of LPS and 39K OMP is highly selective for this protein and does not involve other proteins). The inherent toxicity of native LPS moieties of most gram-negative bacteria precludes the utilization of an intact LPS molecule as a vaccine in infants.

There, therefore, remains a need for a monoclonal antibody which recognizes more, if not all known, strains of *H. influenzae* type b and, at the same time, does not recognize other organisms or material which may be found in conjunction with *H. influenzae* type b. There also remains the need for a means for diagnosis of *H. influenzae* type b infections which is fast, specific and sensitive without giving false positive indications of infection.

SUMMARY OF THE INVENTION

The present invention provides a monoclonal antibody reactive with an epitope of a surface component of the bacterium *Haemophilus influenzae* type b, said monoclonal antibody being reactive with a surface component present in at least 95% of strains of said bacterium.

Preferably such a monoclonal antibody is reactive with an epitope of an outer membrane protein, especially a protein of about 37,000 daltons of *H. influenzae* type b.

Another aspect of this invention provides a cell line capable of producing a monoclonal antibody reactive with an epitope of a surface component of the bacterium *Haemophilus influenzae* type b, said epitope of said surface component being present in at least 95% of strains of said bacterium.

Preferably such a cell line is capable of producing a monoclonal antibody reactive with an epitope of an outer membrane protein of *H. influenzae* type b. Preferably the cell line is a hybridoma cell line, especially a hybrid of a mouse spleen cell and a myeloma cell.

In another aspect this invention provides a method of identifying, serotyping or detecting the presence of the bacterium *Haemophilus influenzae* type b or antigens of said bacterium which comprises: (a) contacting a sample suspected of containing said bacterium or antigens of said bacterium with such a monoclonal antibody and, if required, a substantially purified surface component reactive with said monoclonal antibody; and (b) observing whether cell-labelling, agglutination occurs or inhibition of agglutination, positive cell-labelling, agglutination or inhibition of agglutination respectively indicating the presence of said bacterium or antigens of said bacterium.

Preferably such a method employs a monoclonal antibody reactive with an outer membrane protein present in at least 95% of strains of such a bacterium. It is further preferred that the label is selected from a radiolabel, a fluorescence label and an enzyme label and a biotin label. Such a method may also be used to detect infection of the bacterium *Haemophilus influenzae* type b in a patient.

A further aspect of this invention provides a kit for determining the presence of the bacterium *Haemophilus influenzae* type b comprising a carrier being compartmented to receive at least two vials and to maintain said vials in close confinement which comprises: (a) a first vial containing such a monoclonal antibody; and (b) a second vial containing detection means whereby interactions between said monoclonal antibody and the bacterium or an antigen of the bacterium may be detected.

A further aspect of the invention also provides a kit for identifying, serotyping or determining the presence of the bacterium *Haemophilus influenzae* type b or an antigen of said bacterium which comprises: (a) a reagent containing such a monoclonal antibody; and, (b) detection means whereby interactions between said monoclonal antibody and the bacterium or an antigen of the bacterium may be detected.

In kits of these types it is preferred that the first vial contains a monoclonal antibody reactive with an outer membrane protein present in at least 95% of strains of such a bacterium. Especially preferred are kits containing a Hb-1, Hb-2 or Hb-5 monoclonal antibody or a monoclonal antibody raised against an epitope of a 37,000 dalton outer membrane protein of such a bacterium, the epitope of the outer membrane protein being found in at least 95% of strains of the bacterium.

In kits of these types it is preferred that the detection means has a label selected from a radiolabel, a fluorescence label and an enzyme label and a biotin label. The detection means may comprise ELISA, dot enzyme immunoassay, liquid or solid phase RIA, latex agglutination, coagglutination or means to inhibit ELISA, dot enzyme immunoassay, liquid or solid phase RIA, latex agglutination or coagglutination. Such kits may further include, as part of the detection means, a substantially purified antigen reactive with the monoclonal antibody contained in the kit. In such kits the detection means may be held in the solid phase.

A further aspect of this invention provides an outer membrane protein of the bacterium *Haemophilus influenzae* type b having an epitope present in at least 95% of strains of the bacterium, or a fragment of the outer membrane protein containing the epitope, in substantially pure form. A preferred embodiment of this aspect of the invention is a 37,000 dalton protein or fragment thereof containing such an epitope. It is to be preferred that such an epitope is present only in *H. influenzae* type b and is also present in all, or substantially all, i.e. more than 99% of strains of *H. influenzae* type b.

We have generated MAbs directed against several OMPs of *H. influenzae* type b and identified corresponding specific OMPs. One of these MAbs defines a surface component common to all strains of *H. influenzae* type b. The use of this MAb for immunodiagnosis and serotyping of *H. influenzae* type b is disclosed.

DETAILED DESCRIPTION OF THE INVENTION

The production of a monoclonal antibody directed against a serotype-specific outer membrane protein of *H. influenzae* type b.

Bacterial strains and culture conditions. Encapsulated *H. influenzae* strains type a to f, and untypable H. influenzae strains were obtained from clinical isolates from Sainte-Justine Hospital, Montreal, the Montreal Children's Hospital, Montreal, Vancouver Children's Hospital, Vancouver, Provincial Laboratory of Public Health of Alberta, Edmonton, Children's Hospital of Eastern Ontario, Ottawa, Laboratoire de la Santé Publique du Québec, Sainte-Anne de Bellevue, and Centre Hospitalier Universitaire de Laval, Sainte-Foy. The strains were identified by their requirements for both X and V factors and strain type was determined by slide agglutination with commercially available sera (Difco Laboratories, Detroit, Mich.). *H. influenzae* was grown overnight at 37° C., in an atmosphere containing 5% $CO_2$, on chocolate agar plates supplemented with 1% ISOVITALEX* (BBL, Cockeysville, Md.). Cultures were stored at −70° C. in brain heart infusion broth containing 20% glycerol or kept lyophilized in skim milk.
Trade Mark Outer membrane preparation. The extraction of outer membrane from the bacteria was performed as described by Johnston et al., J. Exp. Med., 143, 741-758 (1976) with slight modifications. Whole cells were suspended in lithium chloride buffer (200 mM lithium chloride, 100 mM lithium acetate, pH 6.0) and the bacteria were shaken with 6 mm glass beads at 300 rpm for 2 h at 45° C. The spheroplasts were removed by centrifugation at 15,000×g for 20 min and the supernatant was collected and centrifuged at 40,000 ×g for 2 h. The pellet was washed once and then resuspended in phosphate buffered saline (PBS). The protein content was determined by the BIO-RAD* protein assay (Bio-Rad Laboratories, Mississauga, Ontario, Canada).
Trade Mark Immunization of mice. BALB/c mice were innoculated intraperitoneally and in the foot pads with 50 ug of *H. influenzae* type b strain 3068 OMPs suspended in Freund's incomplete adjuvant (Gibco Laboratories, Grand Island, N.Y.). Four weeks later, the mice were reinjected intravenously with 30 μg of OMPs suspended in PBS. Four days before the hybridoma production, the immunized mice received another intravenous injection of 30 /ug of OMPs. Sera were obtained from the immunized mice by cardiac puncture before the spleen was removed.

Fusion procedure. Hybridomas were produced according to the methods of De St. Groth and Scheidegger, J. Immunol Methods, 35, 1-21 (1986) with modifications. Spleen cells from immunized mice and nonsecreting, HGPRT deficient, mouse myeloma cells SP2/0 were fused in a ratio 10μl in Dulbecco modified Eagle's medium (DMEM, Flow Laboratories, Mississauga, Ontario, Canada) containing 50% (w/v) polyethylene glycol 1000 (T. J. Baker Chemical Co., Phillipsburg, N.J.). The myeloma cells were cultured in the presence of 20 /μM 6-thioguanin for 5 to 7 days before the fusion. The fused cells (0.1 ml, 105 cells/ml) were dispensed in 96-well tissue culture plates (Costar plastics, Vineland, N.J.) which already contained a feeder layer of $7\times10^3$ murine peritoneal exudate cells. The cell suspensions were grown in DMEM supplemented with 20% fetal calf serum (Gibco), 2 mM L-glutamine (Sigma Chemical Co., St-Louis, Mo.) and 50 μg/ml gentamicin (Sigma) in the presence of hypoxanthine, aminopterin and thymidine (HAT) selection medium. On days 5 and 6 all cultures were checked for the presence of clones and the medium was changed on day 7 with HT instead of HAT. On days 10 to 12, supernatants of wells containing growing clones were tested by ELISA for MAb directed against *H. influenzae* type b outer membrane antigens. The antibody-producing cells were subcloned by limiting dilution. Selected subclones were grown either in vitro for freezing in liquid nitrogen or as ascites according to the method of Brodeur et al, J. Immunol Methods, 71, 265-272 (1984).

Determination of immunoglobulin class. The supernatant from antibody producing cells were tested against isotype and subclass specific antisera (Meloy, Springfield, Va.) using the Ouchterlony double diffusion method.

Enzyme-Linked Immunosorbent Assay (ELISA) Procedure. The screening of supernatants for the presence of MAbs directed against *H. influenzae* was performed as descrieed by Brodeur et al, J. Med. Microbiol., 15, 1-9, (1982). A volume of 0.1 ml of outer membrane antigen containing 0.25 μg protein in 0.05M carbonate buffer pH 9.6 was dispensed in each well of a LINBRO* E.I.A.
microtiter plate (Flow). The plate was incubated for 18 h at room temperature to allow the adsorption of the antigen and then washed with PBS containing 0.02% Tween-20 (Sigma). A volume of 0.2 ml 0.1% bovine serum albumin (BSA, Sigma) in PBS was then added to each well. After incubating the plate for 30 min at 37° C., the BSA was discarded and the plate was washed and the test supernatants were added. A standard serum was used as positive control. After incubation for 1 h at 37° C., the plate was washed thrice before the addition of 0.1 ml alkaline phosphatase-conjugated goat anti-mouse immunoglobulins (Miles Laboratories, Elkart, Ind.) diluted 1:1000 in PBS containing 3% BSA. After another 1 h incubation at 37° C., the plate was washed and 0.1 ml of a 10% diethanolamine solution at pH 9.8, containing 1 mg/ml p-nitrophenylphosphate (Sigma) was added. Sixty minutes later, the absorbance was determined spectrophotometrically at 410 nm using a DYNATECH* microplate reader MR 600. A reading greater than 0.2 was scored as positive for the presence of antibodies directed against *H. influenzae* type b outer membrane antigens. Background level of absorbance with control SP2/0 culture supernatant was always lower than 0.050.

* Trade Mark

SDS-polyacrylamide gel electrophoresis (PAGE). OMPs were resolved by electrophoresis on sodium dodecyl sulfate (SDS) 1.5 mm thick slab gels according to the method of Laemmli, Nature, 227, 680–685 (1970). A 10% acrylamide (Bio-Rad) resolving gel and a 4.0% stacking gel were used. The samples were prepared by mixing one part of outer membrane antigens (1 mg protein/ml) with four parts of the sample buffer (62.5 mM Tris-HCl pH 6.8, 1% (v/v) glycerol, 2% (w/v) SDS, 0.5% (v/v) 2-mercaptoethanol and 0.5% (w/v) bromophenol blue) and heated for 4 min at 100° C. Aliquots of 80/$\mu$l containing 20–25/$\mu$g of protein were applied to each gel lane. Electrophoresis was carried out at 20 V/gel constant voltage until the bromophenol blue tracking dye entered the separating gel at which time the voltage was increased to 30 V/gel. The gels were stained with Coomassie blue dye and then destained as described by Weber and Osborn in J. Biol. Chem. 244, 4406–4412 (1969). The following proteins were used as molecular weight standards: myosin (200,000), phosphorylase b (92,500), bovine serum albumin (68,000), ovalbumin (43,000), $\alpha$-chymotrypsinogen (25,700), $\beta$-lactoglobulin (18,400) and cytochrome C. (12,300) (Bethesda Research Laboratories, Gaithesburg, Mass.).

Immunoblotting procedure. Following SDS-PAGE, the proteins were transferred electrophoretically from the gel to nitrocellulose paper (Bio-Rad) by the method of Towbin et al. in Proc. Natl. Acad. Sci. U.S.A., 76, 4350–4354 (1979). A constant potential of 40 V (5 V/cm) was applied to the gel-nitrocellulose paper sandwich for 1.5 h in an electroblot buffer consisting of 25 mM Tris-HCl, 192 mM glycine and 20% (v/v) methanol at pH 8.3. The transferred proteins on the blot were either stained with amido black or detected by an enzyme immunoassay. To detect bacterial antigens, the paper was soaked in PBS solution containing 3% BSA for 30 min to block non-specific protein binding sites, and then incubated for 1 h at 37° C. with mouse hyperimmune sera or ascitic fluids diluted 1:100 in PBS containing 3% BSA. The sheet was washed thrice with PBS and incubated with peroxidase-conjugated goat anti-mouse immunoglobulins (Cappel, Cochranville, Pa.) diluted 1:1000 in PBS containing 3% BSA. After 1 h incubation at 37° C. and three washes, the blots were soaked in a solution of o-dianisidine prepared as described by Towbin et al. (op cit). A radioiodinated protein-A binding assay was used to detect MAb Hb-2 following the transfer. The nitrocellulose paper was soaked for 30 min at room temperature in PBS containing 5% (w/v) skim milk (Carnation*). The blot was then incubated overnight at 4° C. with mouse hyperimmune sera or MAb Hb-2 diluted in skim milk solution. The blot was washed for 10 min in PBS, followed by two more washes in PBS containing 0.05% (v/v) Nonidet P-40* and rinsed for 10 min in PBS. The blot was then soaked for 30 min at room temperature in skim milk solution containing 0.25 $\mu$ci per ml of protein-A labelled with $^{125}$iodine (New England Nuclear, Boston, Mass). After four washes as described above, the sheet was exposed at −70° C. to Kodak XAR-5 film using a Kodak X-OMATIC cassette fitted with intensifying screens.

* Trade Mark

Dot-enzyme immunoassay. A dot-enzyme immunoassay was used for rapid screening of several MAbs against a large number of *H. influenzae* strains. The bacterial strains were grown overnight on chocolate agar plates and an inoculum of approximately $10^9$ bacteria/ml was prepared in PBS. A small amount of the suspension, 5 $\mu$l, was applied to a nitrocellulose paper and allowed to dry at room temperature. The dot-nitrocellulose paper was then processed as described in the immunoblotting procedure.

Adsorption of monoclonal antibody. Twofold dilutions of hybridoma supernatants (0.2 ml) were mixed with $10^9$ live intact *H. influenzae* cells kept in the cold or organisms killed by treatment with 0.5% formalin in PBS. The suspensions were incubated either for 1 h at 37° C. or 3 h at 4° C. and then centrifged. The resulting supernatants were tested for MAb activity by ELISA.

Enzymatic treatment of OMPs. For protein digestion, 25 $\mu$g of proteinase K (Boehringer Mannheim GmbH, West Germany) or 150 $\mu$g of protease from Streptomyces griseus type VI (Sigma) in PBS was added to 15 $\mu$l (1 mg of protein /ml) of outer membrane preparation of *H. influenzae* type b strain 3068. After 1 h incubation at 37° C., the OMP concentration was adjusted to 2.5$\mu$g/ml with carbonate buffer, and 0.1 ml of the solution was dispensed into each well of a Linbro E.I.A. microplate, and allowed to adsorb for 60 min at 37° C. The supernatants were tested by ELISA as described. The supernatants tested against proteinase K or protease treated-OMPs were collected and retested against untreated outer membrane preparations as control for possible residual enzymatic activity.

Other membrane protein profiles of *H. influenzae*. We examined by SDS-PAGE the polypeptide composition of the outer membrane of several clinical isolates of *H. influenzae* type b obtained from patients at Sainte-Justine Hospital. Large amounts of OMPs were extracted using the lithium chloride procedure which did not require sonication or treatment with detergent. The bacterial cell wall was not destroyed, thus, avoiding any release of cytoplasmic components. All type b strains had a similar pattern of protein migration and each strain contained major OMPs with apparent molecular weights of 43,000, 39,000, 37,000 and 27,000 daltons. In some strains, the 39,000 and 37,000 molecular weight proteins were separated into two polypeptides. The presence of the 39,000 dalton protein was vaguely discernable in some strains and not detectable in one strain tested. The preparation of outer membranes of *H. influenzae* type b strain 3068 was selected as immunogens for hybridization because this preparation has demonstrated a regular and typical pattern in migration of the major OMP's on SDS-PAGE. The OMPs were selected to be used in the screening of MAbs because they represented the major variations in the patterns of OMPs of *H. influenzae* type b.

Properties of monoclonal antibodies. More than 340 hybrid clones were obtained by fusing sensitized spleen cells with SP2/0 plasmacytoma cells. The screening for MAbs in hybridoma culture supernatants was performed by ELISA, using the homologous immunizing *H. influenzae* type b strain 3068 outer membrane preparations as coating antigens. Each positive hybrid clone supernatant was further tested against several heterologous type b and untypable *H. influenzae* strains. Eleven hybridoma cell lines showing different patterns of reactivity in ELISA were obtained (Table I). There were several MAbs which showed a stronger ELISA response against heterologous *H. influenzae* strains than against the immunizing homologous strain 3068. MAbs Hb-1, Hb-2 and Hb-5 reacted specifically with *H. influenzae* type b while other MAbs cross-reacted with type b and untypable strains. Hybridomas producing MAbs directed against OMPs of *H. influenzae* were subcloned twice by limiting dilution and the class and subclass of these immunoglobulins were determined by gel immunodiffusion. One MAb, HI-1 was an IgM, whereas all other MAbs were IgG's.

Monoclonal antibody reactivity with proteolytic enzyme treated-OMPs. Outer membrane preparations of homologous immunizing strain were incubated with proteinase K or protease before being used as coating antigens in an ELISA assay. These treatments altered the OMP structures. As a result, the MAb reactivities in the ELISA assay could not be detected. When these TABLE I
CHARACTERIZATION OF MONOCLONAL ANTIBODIES DIRECTED AGAINST *HAEMOPHILUS INFLUENZAE* OUTER MEMBRANE PROTEINS

| MAbs | IMMUNO-GLOBULIN CLASS/SUBCLASS | REACTIVITY WITH | |
|---|---|---|---|
| | | TYPE B[a] | UNTYPABLE[a] | OMP[b] |
| HI-3 | IgM | 9/15 | 2/5 | negative |
| HI-4 | IgG | 14/15 | 0/5 | 43,000 |
| Hb-5 | IgG$_2$a | 15/15 | 0/5 | negative |
| HI-6 | IgG$_2$a | 11/15 | 0/5 | negative |
| HI-7 | IgG$_2$b | 10/15 | 5/5 | 13,000 |
| Hb-1 | IgG$_1$ | 15/15 | 0/5 | 37,000 |
| Hb-2 | IgG$_2$a | 15/15 | 0/5 | 37,000 |
| HI-8 | IgG$_3$ | 12/15 | 2/5 | negative |
| HI-9 | IgG$_2$a | 7/15 | 2/5 | 37,000 |
| HI-10 | IgG$_2$b | 15/15 | 5/5 | 13,000 |
| HI-11 | IgG$_3$ | N.D.[c] | N.D. | N.D. |

[a]Number of positive/Number of strains tested by ELISA
[b]Immunoblotting technique
[c]N.D. - Not done MAbs were retested against non-treated OMPs the absorbance values were positive (Table II). MAb HI-11, when tested against proteinase K treated OMPs, still, demonstrated activity. However, when tested against the OMPs treated with protease the MAb HI-11 reactivity was not detected. Furthermore, we have purified LPS from *H. influenzae* type b and monoclonal antibodies Hb-1 and Hb-2 do not react with this preparation.

Identification of antibody-specific epitopes on the OMPs. The Western immunoblotting technique was used to determine the specific OMPs to which each of the MAbs bind. The mouse hyperimmune serum, used as positive control, detected all the major OMP's present in *H. influenzae* type b strains. Four of the 10 MAbs reacted with OMPs transferred from the SDS-PAGE to nitrocellulose sheets. Three different OMPs with apparent molecular weights of 43,000, 37,000 and 13,000 daltons were recognized by the MAbs HI-4, HI-9 and HI-7 respectively. MAb HI-10 reacted with a low molecular weight band (13,000 daltons) not visible on the Coomassie blue stained gel or the amido black stained nitrocellulose paper.

Five other MAbs did not react on immunoblots. The MAbs Hb-1 and Hb-2 which recognized all strains of *H. influenzae* type b, were among those not reacting. Efforts were made to restore their reactivity because these MAbs are serotype—specific and could be useful as diagnostic reagents. Treatment with anionic TABLE II
MONOCLONAL ANTIBODY REACTIVITY WITH OMPs TREATED WITH PROTEINASE K

| | ELISA VALUE[a] | | |
|---|---|---|---|
| HYBRID-OMA SUPER-NATANT | NON-TREATED OMPs | PROTEIN-ASE K TREATED OMPs[b] | NON-TREATED[c] OMPs |
| HI-3 | 0.562 | 0.014 | 0.411 |
| HI-4 | 0.508 | negative | 0.240 |
| Hb-5 | 0.384 | negative | 0.394 |
| HI-6 | 0.340 | negative | 0.404 |
| HI-7 | 0.318 | negative | 0.227 |
| Hb-1 | 0.607 | negative | 0.494 |
| Hb-2 | 1.823 | negative | 0.964 |
| HI-8 | 0.776 | 0.030 | 0.527 |
| HI-9 | 0.190 | negative | 0.174 |
| HI-10 | 0.387 | negative | 0.215 |
| HI-11 | 0.764 | 0.226 | 0.610 |
| HI-11 | 1.011 | 0.044[d] | 0.900 |

[a]ELISA value: Absorbance (410 nm) after 1 h at room temperature. Control SP2/0 supernatant (0.035) was automatically subtracted from each value.
[b]MAbs were also reacted against OMPs treated with protease and similar results were obtained.
[c]After 1 h at 37° C. the supernatant from proteinase K treated OMPs was transferred to wells coated with non-treated OMPs.
[d]The OMPs were treated with protease.

(sodium deoxycholate) or zwitterionic (EMPIGEN BB*) detergent did not restore the reactivity of the protein to which MAb Hb-1 and Hb-2 bind. The Hb-2 specific OMP could only be revealed by the use of $^{125}$I-labelled protein-A autoradiography. Hb-2 recognized an epitope on the 37,000 dalton OMP. No reaction was demonstrated with MAb Hb-1, an IgG1, using the same procedure. SP2/0 induced ascitic fluids or SP2/0 culture supernatants were negative on immunoblots.
*Trade Mark Binding properties of monoclonal antibody Hb-2. To determine whether MAb Hb-2 was directed against a cell surface-exposed epitope of the 37,000 dalton OMP, dilutions of culture supernatant were incubated with intact homologous or heterologous *H. influenzae* cells. The supernatants were tested by ELISA and compared with unadsorbed controls. The results obtained showed that the absorption of Hb-2 either with the homologous or the heterologous *H. influenzae* type b strains resulted in a complete removal of the antibody. Hb-2 supernatants adsorbed with untypable *H. influenzae* strain gave the same results as the nonadsorbed supernatants. Immunofluorescence assay also suggested that Hb-2 was directed against a cell surface-exposed antigenic determinant.

Specificity of monoclonal antibody Hb-2. The initial characterization by ELISA showed that Hb-2 reacted only with *H. influenzae* type b strains. A dot-enzyme immunoassay was used for rapid screening of this MAb against numerous bacterial strains. The MAb Hb-2 reacted specifically with 326 Canadian strains of *H. influenzae* type b, but not with *H. influenzae* strains of other serotypes or any untypable strains (Table III). Similarly, Hb-2

TABLE III
SPECIFICITY OF MONOCLONAL ANTIBODY Hb-2

| BACTERIAL STRAINS | REACTIVITY[a] |
|---|---|
| H. influenzae type b | 326/326 |
| H. influenzae type a, c-f | 0/40 |
| H. influenzae untypable | 0/86 |
| H. parainfluenzae | 0/6 |
| N. meningitidis | 0/22 |
| S. pneumoniae | 0/30 |
| S. pyogenes group B | 0/20 |
| E. coli | 0/12 |

[a]Number of positive/Number of strains tested by a dot-enzyme immunoassay showed no cross-reactivity with H. parainfluenzae, Escherichia coli, Neisseria meningitidis, Streptococcus group B or Streptococcus pneumoniae strains tested.

Several methods of preparations of outer membranes have been described. The procedure to obtain partially purified OMPs described by Johnston et al. (op. cit.) has the advantage of eliminating the sonication procedure or treatment with detergents, thus preventing the breakage of the bacterial cell wall and avoiding contamination of the preparation with cytoplasmic bacterial components. The lithium chloride method resulted in a more effective extraction of outer membrane of H. influenzae. All strains of H. influenzae type b had SDS-PAGE patterns of OMPs typical of other gram-negative bacteria described. Furthermore, when these OMPs are used to produce hyperimmune sera in mice, 9 major proteins are always detected by immunoblotting and $^{125}$I-labelled protein-A autoradiography. Examination of the protein patterns confirmed the variability of the 39,000 and 38,000 dalton proteins. These proteins were present in varying quantities in related strains and were undetectable in other strains. The 37,000 dalton protein was present in all strains and sometimes appeared as two proteins.

Analysis of the antigenic composition of the OMPs of H. influenzae type b has been encouraged by recent works which demonstrated that MAbs directed against specific OMPs of gram-negative bacteria can protect against systemic infections in animals. For the investigation of these proteins as potential vaccine candidates, it is important that a common epitope or an antigenically cross-reactive determinant on the OMPs be identified. Antigenic relatedness has already been demonstrated in other organisms using MAbs. Eleven MAbs were selected for this study based on their patterns of reactivity against different strains of H. influenzae type b in ELISA. Specific OMPs to which 5 of the MAbs bind were identified by Western blotting followed by enzymatic immunodetection or $^{125}$I-labelled protein-A autoradiography. The remaining MAbs failed to react in either system of detection, even though they were reactive in ELISA test. The enzymatic treatment of OMPs with proteinase K and protease clearly demonstrates that the MAbs were directed against a protein antigenic determinant.

Different MAbs directed against H. influenzae type b OMPs are already known. In one case, only 61.8% of the strains were identified by an antibody directed against a 100,000 dalton protein. Recently, a MAb reacting with a 98,000 dalton protein recognized 83 of the 120 H. influenzae type b strains tested. The MAb Hb-2 reacted with all 326 strains of H. influenzae type b tested in a dot-enzyme immunoassay. A MAb reacting with an accessible surface-exposed epitope present on all H. influenzae type b strains would be useful for the development of a diagnostic test for H. influenzae type b infections or the identification of common antigenic determinants for the development of OMP vaccine. Binding assays as well as immunofluorescence data demonstrated that MAb Hb-2 recognized a cell surface-exposed antigenic determinant. Western immunoblotting followed by $^{125}$I-labelled proteinA autoradiography revealed that the MAb Hb-2 reacted specifically with a 37,000 dalton protein common to all H. influenzae type b strains. This is the first report of a single murine MAb, directed against an OMP, which recognizes a cell surface-exposed antigenic determinant common to known H. influenzae type b strains. We have also tested the MAb Hb-2 against Neisseria meningitidis, Streptococcus group B, Streptococcus pneumoniae, Escherichia coli strains and a number of untypable H. influenzae strains and none of these bacteria reacted with Hb-2. There is considerable interest in the use of MAb Hb-2 in immunodiagnostic procedures for the detection of microbial antigens in clinical specimens. We have evaluated the usefulness of biotinylated MAb Hb-2 and avidin-peroxidase in a capture assay for the rapid detection of H. influenzae antigens in cerebrospinal fluid, serum and urine of children with severe infections.

Diagnosis of the presence of Haemophilus influenzae type b

The rapid detection of soluble bacterial antigens in the body fluids of patients presenting with severe infections has distinct clinical advantages. A positive result can allow a more precise and rapid antimicrobial therapy. The result of the antigen detection is available at least 18 hours before the result of the culture, and especially useful when Gram staining and culture remain negative.

A variety of tests have already been used for bacterial antigen detection. These include counterim unoelectrophoresis, latex agglutination, co-agglutination and Enzyme Linked Immunosorbent Assay (ELISA). The immunodiagnostic reagents used for the detection of H. influenzae type b (Hib) antigen are usually limited by a problem of an unsatisfactory sensitivity and of a low specificity. Most of the limitation of these tests are due to the non-specificity of the polyclonal antisera used. Some contaminants may persist in the extract used as immunogen, despite a rigorous purification. Alternatively, antibody preexisting from previous natural infection may be present in the serum of the hyperimmunised animal and give rise to false positive reactions. A new era in serology was promoted by hybridoma technology, from which monoclonal antibodies are produced and could reduce at a minimal level the incidence of cross-reactivity among bacterial antigens and consequently increase the specificity of these tests.

This aspect of the invention concerns the detection of bacterial antigens, namely polyribose phosphate (PRP) and outer membrane proteins (OMP), in the body fluids collected from children presenting with a severe infection due to H. influenzae type b. An enzyme immunoassay using both rabbit polyclonal and murine monoclonal antibodies will permit to compare the sensitivity and the specificity of this new assay with three other methods, including latex agglutination "LA-BACTIGEN*", coagglutination "CoA-Phadebact*", and counterimmunoelectrophoresis (CIE).

*Trade Mark

Clinical specimens and bacterial strains. CSF, sera and urine specimens were collected from children admitted to Sainte-Justine Hospital (Montreal, Canada) from January 1984 to February 1985, with a proven diagnosis of H. influenzae type b infection as detected by culture or in 2 different serological tests. The specimens were processed for Gram staining and culture on chocolate agar plates. If they were not subjected to antigen testing immediately, the specimens were kept frozen at −70° C.

Monoclonal antibody production and purification. BALB/c mice were injected intraperitoneally and in the foot pads with an extract of 50 g outer membrane proteins (OMPs) from H. influenzae type b mixed with Freund's incomplete adjuvant. Four weeks later, mice were immunized intravenously with 30 µg of OMPs suspended in PBS. Four days before the hybridoma production, the mice received the last intravenous injection of 30 µg of OMPs. Monoclonal antibodies against OMP were obtained by fusing sensitized spleen cells with the non-secreting mouse myeloma cells SP2/0 as described above. The antibody-producing cells were cloned twice by limiting dilution, and ascitic fluids were produced in mice according to the procedure described by Brodeur et al (op. cit.). Antibody class and subclass were determined by double radial immunodiffusion. Culture supernatants were concentrated 10 times by ammonium sulfate precipitation and tested against rabbit antimouse immunoglobulins γ1, γ2a, γ2b, γ3 and µ heavy chain antisera mouse immunoglobulins (Meloy, Springfield, Va.).

Ascitic fluids containing MAb Hb-1 was passed throgh a glasswool and treated by AEROSIL* 380 (Degussa, West-Germany) 20 mg per ml of ascitic fluids in order to remove the β-lipoproteins. The mixture was stirred for 4 hours at room temperature, and the precipitate was removed by centrifgation at 12,000×g for 30 min. The treated ascitic fluids were applied on AFFI-GEL* Protein A MAPS Kit (Bio-Rad Laboratories, Richmond, Calif.). The concentration of the IgG proteins was determined spectrophotometrically at 280 nm.
*Trade Mark Polyclonal rabbit antiserum directed against PRP was purchased from the New-York State Department of Health, Division of Laboratories and Research, Albany, N.Y.

Biotinylation procedure. Biotin was covalently conjgated to purified preparation of MAb Hb-1 and normal mouse IgG (NMIgG) by a modification of the method described by Bayer and Wilcheck (Methods Enzymol. 34, 265–267 (1974)). Briefly, biotin (BIO-CAP-NHS*, Calbiochem-Behring) was dissolved in dimethylformamide at variable concentrations. A volume of 100 µl of each dilution was added to 1 ml of IgG diluted to a concentration of 3 mg/ml in phosphate-buffered saline (PBS) at pH 7.2. The reaction mixture was rocked for 3h at 25° C. and dialysed at 4° C. against two changes of PBS. After dialysis, an equal volume of glycerol was added and the biotinylated MAb and NMIgG preparations (b-MAb) were stored at −20° C.
*Trade Mark Biotin-Avidin Enzyme Immunoassay (B-A EIA). All assays were performed in rigid, non-sterile flatbottomed microtiter plates (IMMULON II*, Dynatech Laboratories, Alexandria, Va.). Wells were coated overnight at room temperature with 200µl of rabbit anti-PRP (1 µg/ml) suspended in 0.1M sodium bicarbonate pH 9.6, and postcoated with 300 µl of PBS-TWEEN 20 (Polyethylene Sorbitan Monolaurate)* (0.05%) containing 2% bovine serum albumin (BSA), and 1% L-lysine for 30 min. at 37° C. The plates were kept at −20° C. until used. Before use the coated plates were washed three times with PBS-TWEEN 20 (Polythylene Sorbitan Monolaurate). Clinical specimens of CSF, serum and urine were diluted 1:2 in PBS-TWEEN 20 (Polythylene sorbitan monolaurate) and a volume of 200 µl was added to each well. The plates were incubated for 2 hours at 37° C., followed by three washes with 250 µl of PBS-TWEEN 20 (Polythylene Sorbitan Monolaurate). Each specimen had two wells treated with (biotin-leaked) b-NMIgG and two with b-MAb (2 µg/ml). After an incubation of one hour at 37° C., the plates were washed 3 times, and a volume of 200 µl of avidin-peroxidase (Sigma) diluted 1:1000 was added, and the plates were incubated for 20 min. at room temperature and then washed. A volume of 200 µl of 5-aminosalicylic acid (80 mg dissolved in distilled water at 70° C., cooled to 25° C., and adjusted at pH 6 with NaOH) containing 0.0025% $H_2O_2$ was added. After 30 min. at room temperature, the absorbance value at 490 nm for each well was determined on micro-ELISA reader (MR 600*; Dynatech). Test was considered positive if the absorbance value was 3 standard deviations greater than the mean absorbance of the negative control (clinical specimens collected from patients who had no well documented previous exposure to Hib).
*Trade Mark Latex agglutination (LA) test. The "BACTIGEN" test (Wampole Laboratories) was used to test CSF, sera and urine specimens. These samples were tested according to the instructions of the manufacturer with the Haemophilus antibody latex and control latex reagents. The CSF were not heat treated, but cloudy or bloody specimens were centrifged for 10 min at 1,000×g before testing.

Coagglutination (CoA) test. The "PHADEBACT" Haemophilus test was purchased from Pharmacia Diagnostics (Uppsala Sweden). All the CSF specimens, from both positive or negative culture, were tested with each of the following reagents: H. influenzae type b; H. influenzae types a, c, d, e and f; S. pneumoniae; and group B Streptococcus. Before testing, each specimen was heated at 80° C. for 5 min. to eliminate nonspecific reactions. CoA results were recorded as positive if a significantly stronger and more rapid reaction occurred with any of the test slide at the same time. Results were considered negative if no agglutination was observed with any of the test reagents. The results were considered to be noninterpretable if the CoA occurred at equally strong intensity and speed with more than one reagent.

Counterimmunoelectrophoresis test (CIE). CIE was performed with Hib antiserum (Staten Serum-Institut, Copenhagen, Denmark). Clinical specimens (CSF, serum and urine) and antiserum were placed in 5-mm wells spaced 3 mm apart on a 1% agarose coated glass slide. The slides were electrophoresed in a barbital buffer (pH 8.6) for 90 min. at 30 mA. The presence of sharp precipitin band was interpreted as positive. Plates showing broad precipiting bands were soaked in normal saline overnight and observed again the following day.

Properties of monoclonal antibody. Monoclonal antibody Hb-1 was screened against different Hib strains by a dot-enzyme immunoassay performed as described. Hb-1 reacted specifically with 276 strains of Hib but not with the other serotype or untypable strains. The characterization of Hb-1 (IgG1) by Western immunoblotting analysis revealed that it is directed against the 37,000 dalton OMP.

Sensitivity. The optimal binding ratio of biotin to monoclonal antibody Hb-1 that yield the highest sensitivity in B-A EIA was found to be 1 mg of biotin for 3 mg of antibody. The sensitivity of the B-A EIA assay was evaluated using serial dilution of *H. influenzae* type b organism. The minimum number of bacteria giving a positive reaction with an absorbance value of (0.095) was 50 bacteria per ml.

Specificity. In order to evaluate the specificity of the MAb Hb-1 used in the B-A EIA, we tested a panel of microorganisms ($10^5$ CFU/ml) isolated from children infected by a variety of bacterial strains: Staphylococcus (17 cases), *Streptococcus pneumoniae* (12 cases), *Streptococcus pyogenes* (5 cases), group B *Streptococcus* (17 cases), *Neisseria meningitidis* (11 cases), *Escherichia coli* (9 cases), *H. influenzae* type a, d and e (15 cases) and *H. parainfluenzae* (10 cases). None of these bacteria gave an absorbance value at 490 nm greater than 0.061 (Table IV).

Cerebrospinal fluid. Eighteen CSF specimens collected from 18 children presenting with a meningitis were tested by CIE, two commercial kits (LA-BACTIGEN and CoA-PHADEBACT) and B-A EIA. Among these samples, 12 were positive and 6 were negative by culture; the 6 culture negative CSF had a characteristic Gram stain and *H. influenzae* type b antigens were detected in more than 2 serological tests. A comparative study by these four different methods reveal that the B-A EIA was the most sensitive one for both groups (Table V). Among the CSF positive culture group we found false-negative results which are represented by 4 patients, the first two being negative by the 3 methods, the third negative by LA only, whereas the fourth one was negative by CIE and CoA, and positive by LA. Among the six patients presenting with a negative culture, two gave a false-negative result by CIE.

The specificity of these four serological methods was evaluated by testing 26 CSF specimens collected from 26 pediatric patients presenting with a meningitis caused by a variety of bacteria other than Hib. No false-positive reaction was observed, except on 3 occasions when CIE was positive (*S. pneumoniae*, *E. coli*, and group B *streptococcus*), and on 2 occasions when

TABLE IV

B-A EIA reactivity of the monoclonal antibody Hb-1 against a panel of bacterial strains

| Microorganism[a] | Number of strains tested | Absorbance values at 490 mn (mean ± S.D.)[b] |
|---|---|---|
| PBS-TWEEN 20 (negative control) | | .040 ± .003 |
| Staphylococcus aureus | 8 | .055 ± .019 |
| Staphylococcus epidermidis | 9 | .050 ± .018 |
| Streptococcus pneumoniae | 12 | .061 ± .015 |
| Streptococcus pyogenes | 5 | .050 ± .018 |
| Group B Streptococcus | 17 | .056 ± .018 |
| Neisseria meningitidis | 11 | .060 ± .015 |
| Escherichia coli | 9 | .050 ± .016 |
| Haemophilus influenzae type a | 5 | .055 ± .011 |
| Haemophilus influenzae type d | 5 | .060 ± .016 |
| Haemophilus influenzae type e | 5 | .050 ± .010 |
| Haemophilus parainfluenzae | 10 | .054 ± .019 |
| Haemophilus influenzae type b | 20 | .790 ± .117 |

[a]The bacterial strains were isolated from children and used at a concentration of $10^5$ CFU/ml.
[b]Mean of triplicates ± S.D.

TABLE V

Detection of *Haemophilus influenzae* type b antigens in cerebrospinal fluid

| Test | CSF | Sensitivity[a] % |
|---|---|---|
| Culture | 12/18[b] | 75 |
| CIE | 13/18 | 78 |
| LA-BACTIGEN | 15/18 | 86 |
| CoA-PHADEBACT | 15/18 | 86 |
| B-A EIA | 18/18 | 100 |

[a]Sensitivity: (true positive)/(true positive + false negative).
[b]Number of positive sample/total number. A CSF specimen was considered a true positive when culture or 2 different tests were positive.

LA-BACTIGEN was positive with *S. pneumoniae*, even after heating at 100° C. for 3 minutes. The B-A EIA and the CoA-PHADEBACT were the only 2 methods giving no false-positive result.

Sera. We also tested the sera collected from 8 patients, ged 1 month to 5 years, and presenting with a severe infection due to *H. influenzae* type b. Four of these children had meningitis documented by positive CSF culture in three and characteristic Gram staining in one. Two had epiglottitis, and two had cellulitis (all four documented by positive blood cultures). A first serum was collected after 1 to 4 days of hospitalization. All these pecimens were positive by B-A EIA, 6 by LA-BACTIGEN, and 5 by CIE (Table VI).

In order to evaluate the persistance of the antigen in the circulation, eight sera were collected from the same patients after a period ranging from 3 to 4 weeks of post-therapy period, and tested concomitantly with the sera collected during the acute phase. Five samples remain positive by B-A EIA, whereas LA was positive in only one, and CIE in none (Table VI).

As negative control, we first tested the sera collected from 14 patients during the acute phase of a meningitis due to *S. pneumoniae* (4 cases), *N. meningitidis* (3 cases), group B *Streptococcus* (3 cases) and *E. coli* (4 cases). All these samples were negative by B-A EIA, whereas LA-Bactigen was positive in one (*S. pneumoniae*) and CIE in two (*S. pneumoniae* and *E. coli*). An additional number of 45 sera collected from normal children was evaluated by the B-A EIA and found to be negative. These last sera also permitted to determine the negative control of the assay.

TABLE VI

Detection of *Haemophilus influenzae* type b antigens in acute and convalescent sera

| Patient | Diagnosis | Culture of CSF or Blood | CIE | LA-Bactigen | B-A EIA |
|---|---|---|---|---|---|
| A | Meningitis | + | −/−[a] | +/− | +/+ |
| B | Meningitis | + | +/− | +/+ | +/+ |
| C | Meningitis | + | +/− | +/− | +/+ |
| D | Meningitis | − | +/− | +/− | +/− |
| E | Epiglottitis | + | +/− | +/− | +/+ |
| F | Epiglottitis | + | −/− | −/− | +/− |
| G | Cellulitis | + | +/− | +/− | +/+ |
| H | Cellulitis | + | −/− | −/− | +/− |
| Sensitivity % | | | 89 | 73 | 80 | 100 |

[a]Acute serum/convalescent serum.

Urine. Twelve urine samples were collected from 12 children presenting with meningitis due to *H. influenzae* type b during the acute phase and tested by the four serological methods described. All these specimens were positive by B-A EIA, whereas 11 by LA, 10 by CoA and 8 by CIE (Table VII).

As negative control, we studied urine specimens collected from healthy children (10 cases) and patients (10 cases) presenting with a variety of infectious diseases due to a microorganisms other than Hib. The B-A EIA test was negative for all these specimens, whereas CIE was positive in 2, and LA-BACTIGEN and CoA-PHADEBACT in 1 specimen respectively.

In a first set of experiments, we detected Hib antigens by using a polyclonal antibody produced in rabbit after immunization with whole bacterial strain of Hib as solid phase reagent and a commercial peroxidase-labeled anti-mouse immunoglobulins reacting with the Hib specific MAb (Hb-1). The major disadvantage of this method was a poor sensitivity and reproducibility in addition to a high background activity, i.e. high absorbance values were obtained for normal sera. As a second step, we found that the use of a polyclonal antibody reacting to the PRP as the solid-phase reagent, and a peroxidase labeled MAb (Hb-1) directed against OMP as the liquid-phase reagent give better results. Because the solid phase and liquid phase antibodies are directed at different determinants, this system offers the potential advantage that the binding of antigen to the solid-phase will not result in a decrease in the number of antigenic sites available to

TABLE VII

Detection of *Haemophilus influenzae* type b antigens in urine

| Test | Urine[a] | Sensitivity[b] % |
|---|---|---|
| CIE | 8/12[c] | 75 |
| CoA-PHADEBACT | 10/12 | 86 |
| LA-BACTIGEN | 11/12 | 92 |
| B-A EIA | 12/12 | 100 |

[a]Urine specimens were collected from children who had CSF culture positive for Hib.
[b]Sensitivity: (true positive)/(true positive + false negative).
[c]Number of positive samples/total number.

the liquid-phase antibody. In a final step, we found that the use of a biotinylated MAb (Hb-1) as the liquid phase reagent reacting with the peroxidase linked avidin, still increased the sensitivity of this new assay. This last finding is consistent with other reports describing the advantages of the avidin-biotin immunoassay systems.

The B-A EIA described in this report could detect a number as low as 50 organisms/ml of *H. influenzae* type b grown in a broth culture. When applied to clinical specimens (CSF, serum and urine), this new B-A EIA test gave a greater sensitivity than those obtained by CIE, LA and CoA (Tables V-VII).

In children presenting with a meningitis caused by *H. influenzae* type b and group B Streptococcus, the concentrated urine remained antigen positive after therapy for 20 days by LA (*H. influenzae* type b) and 21 days by CIE (group B *Streptococcus*). In the present study, 5 convalescent sera collected 3 weeks after the acute period remained positive by B-A EIA, whereas only 1 was positive by LA and none by CIE. This significant difference for the detection of the antigens in the convalescent sera of children with either meningitis or another type of infection is in accordance with a greater sensitivity of this new EIA test. The high level of sensitivity of this new test will be very helpful for the management of children presenting at the hospital after receiving antibiotics.

In addition to this high quality of the sensitivity, the B-A EIA test showed an excellent specificity. In fact, no positive reactions were noted in CSF, serum or urine specimens collected from children infected by other bacteria than Hib, or from children without evidence of bacterial infection, whereas on occasions a false positive reaction was found by LA test in 3 3 cases infected by *S. pneumoniae*. Recently Macone et al, J. Clin. Microbiol., 21, 711–714 (1985) reported that five patients infected by a pathogen other than *H. influenzae* type had a positive Bactigen-LA test. These 5 cases were represented by *S. pneumoniae* type 14 (2 cases), *N. meningitidis* group C (1 case), *E. coli* $K_{100}$ (1 case), and *S. aureus* (1 case). In our laboratory, we observed 5 false positive reactions involving *S. pneumoniae* (2 cases), *E. coli* (2 cases) and group B *Streptococcus* (1 case) by using the CIE method. These false positive reactions have also been observed after using an antiserum reacting to PRP (Hib), to *E. coli* (Easter strain $K_{100}$), and to *S. pneumoniae* (type 29). When the CSF specimens were tested by CoA, no false positive results were noted. The bloody CSF specimens or those presenting with a high protein content also react non-specifically with a multiple number of antigen reagents. On few occasions, false positive reactions were mediated by the presence of antistaphylococcal antibody in the serum. Premixing with soluble protein A eliminated most of these nonspecific reactions in such cases. With the commercial kit recommendations, one can find that heating the specimen at 80° C., for 5 min. is required to eliminate these inconclusive reactions. It has also been reported that the use of polyclonal antibodies in EIA system for the detection of Hib antigens could yield a false positive result. Such nonspecific reactions and the methods to minimize them have been reviewed by Yolken Rev. Infect. Dis., 4, 35–68 (1982). On the contrary, the monoclonal antibody used in this new B-A EIA test ensured a highly specific reactivity as demonstrated by the complete absence of false-positive results. This advent of type specific monoclonal antibody to Hib and its use in EIA system provides a new powerful technique capable of detecting Hib antigens in clinical specimens.

Hybridomia cell lines producing monoclonal antibodies are being maintained at Laboratory Centre for Disease Control, Health and Welfare Canada, Ottawa, Ontario, Canada K1A 0L2 and are coded as follows:

| Monoclonal antibody | Cell line number | ATCC number |
|---|---|---|
| Hb-2 | LCDC/H2 | |

It is intended to deposit samples of said cell lines, in the ATCC.

What we claim as our invention is:

1. The Hb-2 monoclonal antibody which has the A.T.C.C. Acession Number HB 10289, and which specifically binds to a surface-accessibel outer-membrane protein antigen of the bacterium *Haemophilus influenzae* type b.

2. The Hb-2 cell line which has the A.T.C.C. accession number HB 10289 and which produces a monoclonal antibody specifically binding to a surface-accessible outer membrane protein antigen of the bacterium *Haemophilus influenzae* type b, said outer membrane protein antigent being present in of between 300 and 326 of the strains of said bacterium.

3. The hybridoma cell line of claim 2, formed by fusing immunized mouse spleen cells and mouse myeloma SP2/0 cells, that produces the Hb-2 monoclonal antibody that specifically binds to a cell-surface exposed outer membrane protein of *Haemophilus influenzae* type b, having a molecular weight of about 37,000 daltons when determined by SDS-polyacrylamide gel electrophoresis under reducing conditions after lithium chloride extraction.

4. A method of detecting the presence of the bacterium *Haemophilus influenzae* type b or antigens of said bacterium with the monoclonal antibody of claim 1 which comprises:
   (a) contacting a sample suspected of containing said bacterium or antigens of said bacterium with said monoclonal antibody optionally in the presence of a substantially purified outer membrane protein antigen that specifically binds said monoclonal antibody, to form an antibody-antigen complex; and
   (b) detecting the presence of said antibody-antigen complex.

5. The method of claim 4 wherein said monoclonal antibody has been produced by a hybridoma cell, said hybridoma cell having a spleen-derived parent immunized by an outer membrane protein antigen.

6. The method of claim 4 wherein detection is by means selected from the group of a radiolabel, a fluorescence label and an enzyme label and a biotin label.

7. A kit for determining the presence of the bacterium *Haemophilus influenzae* type b comprising a carrier being compartmented to receive at least two vials and to maintain said vials in close confinement which comprises:
   (a) a first vial containing the monoclonal antibody of claim 1; and,
   (b) a second vial containing detection means whereby interactions between said monoclonal antibody and the bacterium of an antigen of the bacterium may be detected.

8. The kit of claim 7 wherein detection means has a label selected from the group consisting of a radiolabel, a fluorescence label and an enzyme label and a biotin label.

9. A kit for identifying, serotyping or determining the presence of the bacterium *Haemophilus influenzae* type b or an antigen of said bacterium which comprises:
   (a) a reagent containing the monoclonal antibody of claim 1; and,
   (b) detection means whereby intereactions between said monoclonal antibody and the bacterium or an antigen of the bacterium may be detected.

10. The kit of claim 9 wherein detection means has a label selected from the group consisting of a radiolabel, a fluorescence label and an enzyme label and a biotin label.

11. The kit of claim 9 wherein detection means is selected from the group consisting of ELISA dot enzyme immunoassay, RIA, latex agglutination or coagglutination; or inhibition of ELISA, dot enzyme immunoassay, RIA, latex agglutination or coagglutination.

12. The kit of claim 9 wherein detection means is in solid phase.

13. The kit of claim 9 wherein detection means includes a substantially purified antigen that specifically binds with said monoclonal antibody.

* * * * *